United States Patent
Imperiali et al.

(10) Patent No.: US 7,892,775 B2
(45) Date of Patent: Feb. 22, 2011

(54) FLUORESCENCE ASSAY FOR KINASE ACTIVITY

(75) Inventors: Barbara Imperiali, Cambridge, MA (US); Melissa D. Shults, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 504 days.

(21) Appl. No.: 11/801,921

(22) Filed: May 11, 2007

(65) Prior Publication Data

US 2008/0085529 A1 Apr. 10, 2008

Related U.S. Application Data

(60) Division of application No. 10/819,587, filed on Apr. 6, 2004, now Pat. No. 7,262,282, which is a continuation-in-part of application No. 10/681,427, filed on Oct. 8, 2003, now Pat. No. 6,906,194.

(51) Int. Cl.
*C12Q 1/37* (2006.01)
*C07D 215/12* (2006.01)
(52) U.S. Cl. ......................................... 435/14; 546/176
(58) Field of Classification Search .................. None
See application file for complete search history.

(56) References Cited

U.S. PATENT DOCUMENTS

| | | | |
|---|---|---|---|
| 6,310,211 | B1 | 10/2001 | Vaillancourt et al. |
| 6,906,194 | B2 | 6/2005 | Imperiali et al. |
| 7,262,282 | B2 | 8/2007 | Imperiali et al. |
| 7,589,209 | B2 | 9/2009 | Canary et al. |
| 2005/0227365 | A1 | 10/2005 | Canary et al. |
| 2007/0196860 | A1 | 8/2007 | Gee et al. |
| 2008/0009026 | A1 | 1/2008 | Gee |
| 2008/0050761 | A1 | 2/2008 | Imperiali et al. |

FOREIGN PATENT DOCUMENTS

| | | |
|---|---|---|
| JP | 2006/213615 A2 | 8/2006 |
| WO | WO 2005/037859 A2 | 4/2005 |
| WO | WO 2008/016762 A1 | 2/2008 |

OTHER PUBLICATIONS

Royzen, et al., "A Sensitive Probe for the Detection of Zn(II) by Time-Resolved Fluorescence," JACS, 2006, pp. 3854-3855, No. 128.
International Search Report and Written Opinion for International Patent Application No. PCT/US07/76959 dated Oct. 7, 2008.
Carrigan, C.N., et al., "The Engineering of Membrane-Permeable Peptides," *Analytical Biochemistry*, 2005, 341, p. 290-298.
Lindgren, M., et al., "Cell-Penetrating Peptides," *Trends Pharmacol. Sci.*, 2000, 21 p. 99-103.
Newton, A.C., "Protein Kinase C: Structural and Spatial Regulation by Phosphorylation, Cofactors, and Macromolecular Interaction," *Chem. Rev.*, 2001, 2353-2364.

Nishikawa, K., et al., "Determination of the Specific Substrate Sequence Motifs of Protein Kinase C Isozymes," *J Biol. Chem.*, 1997, 272, 952-960.
Ohuchi, Y., et al., "A Fluorescent-Labeled Oligopeptide for Monitoring PKA-Mediated Phosphorylation," *Analyst*, Nov. 2000, 125(11), p. 1905-1907.
Rothman, D.M,. et al., "Chemical Approaches for Investigating Phosphorylation in Signal Transduction Networks," *Trends in Cell Biology*, 2005, 15, No. 9, p. 502-510.
Sainlos, M., et al., "Tools for investigating peptide-protein interactions: peptide incorporation of environment-sensitive fluorophores via on-resin derivatization," *Nature Protocols*, 2007, vol. 2, No. 12, p. 3201-2309.
Sainlos, M., et al., "Synthesis of Anhydride Precursors of the Environment-Sensitive Fluorophores 4-DMAP and 6-DMN," *Nature Protocols*, 2007, vol. 2, No. 12, p. 3219-3225.
Sainlos, M., et al., "Tools for Investigating Peptide-Protein Interactions: Peptide Incorporation of Environment-Sensitive Fluorphores," *Nature Protocols*, 2007, vol. 2, No. 12 p. 3210-3218.
Shults, M.D., et al., "A Multiplexed Homogeneous Fluorescence-Based Assay for Protein Kinase Activity in Cell Lysates," *Nature Methods*, 2005, p. 1-7.
Shults, M.D., et al., "Optimal Sox-BASED Fluorescent Chemosensor Design for Serine/Threonine Protein Kinases," *Analytical Biochemistry*, 2006, p. 198-207, 352.
Shults, M.D., et al. "Versatile Fluorescence Proves of Protein Kinase Activity," *J. Am. Chem. Soc.*, 2003, 125, p. 14248-14249.
Vazquez, M.E., et al., "Photophysics and Biological Applications of the Environment-Sensitive Fluorophore 6-N, N-Dimethylamino-2,3-Naphthalimide," *J. Am. Chem. Soc.*, 2005, 127, p. 1300-1306.
Venkatraman, P., et al., "Fluorogenic Probes for Monitoring Peptide Binding to Class II MHC Proteins in Living Cells," *Nature Chemical Biology*, Apr. 2003, vol. 3, No. 4, p. 222-228.
Wadia, J.S., et al., "Protein Transduction Technology," *Curr. Opin. Biotechnol.*, Feb. 2002, 13(1), p. 52-56.
Wang, Q., et al., "Self-Reporting Fluorescent Substrates of Protein Tyrosine Kinases," *J. Am. Chem. Soc.*, 2006, 128, p. 1808-1809.
Office Action for U.S. Appl. No. 10/681,427, dated Sep. 15, 2004.
Office Action for U. S. Appl. No. 10/819,587, dated Oct. 18, 2006.
International Search Report for Application No. PCT/US2004/032733 dated Apr. 28, 2005.
Written Opinion for Application No. PCT/US2004/032733 dated Oct. 27, 2005.
A list of peptides that can be phosphorylated (and the corresponding Kinases) found at online at www.neb.com/neb/tech/tech_resource/protein_tools/substraye_recognition.html (this website as it existed on Sep. 26, 2003 is provided).
Chien-An, C. et al., "Biosensors of Protein Kinase Action: From In Vitro Assays to Living Cells", *Biochimica et Biophysica Acta*, 1697, pp. 39-51, 2004.
Chien-An, C. et al., "Design and Synthesis of a Fluorescent Reporter of Protein Kinase Activity", *J. Am. Chem. Soc.*, 124, pp. 3840-3841, 2002.

(Continued)

*Primary Examiner*—Zinna N Davis
(74) *Attorney, Agent, or Firm*—Wolf, Greenfield & Sacks, P.C.

(57) ABSTRACT

The present invention provides a sensor and methods for determining kinase activity.

5 Claims, 6 Drawing Sheets

OTHER PUBLICATIONS

Higashi, H. et al., "Imaging of cAMP-Dependent Protein Kinase Activity in Living Neural Cells Using a Novel Fluorescent Substrate", *FEBS Letters*, 414, pp. 55-60, 1997.

Hofmann, R. M. et al., "Fluorescent Monitoring of Kinase Activity in Real Time: Development of a Robust Fluorescence-based Assay for Abl Tyrosine Kinase Activity", *Bioorganic & Medicinal Chemistry Letters*, 11, pp. 3091-3094, 2001.

Kurokawa, K. et al., "A Pair of Fluorescent Resonance Energy Transfer-Based Probes for Tyrosine Phosphorylation of the Crkll Adaptor Protein in Vivo", *The Journal of Biological Chemistry*, 276, No. 33, pp. 31305-31310, 2001.

Lawrence, D., "Chemical Probes of Signal-Transducing Proteins", *Acc. Chem. Res.*, 36, pp. 401-409, 2003.

McIlroy, B. K. et al., "A Continuous Fluorescence Assay for Protein Kinase C", *Analytical Biochemistry*, 195, pp. 148-152, 1991.

Nagai, Y. et al., "A Fluorescent Indicator for Visualizing cAMP-Induced Phosphorylation in Vivo", *Nature America Inc.*, 18, pp. 313-316, 2000.

Post, P. et al., "A Genetically Engineered, Protein-Based Optical Biosensor of Myosin II Regulatory Light Chain Phosphorylation", *The Journal of Biological Chemistry*, 269 No. 17, pp. 12880-12887, 1994.

Sato, M. et al., "Fluorescent Indicators for Imaging Protein Phosphorylation in Single Living Cells", *Nature Biotechnology*, 20, pp. 287-294, 2002.

Shults, M.D. et al., "Versatile Fluorescence Probes of Protein Kinase Activity", *J. Am. Chem. Soc.*, 125, pp. 14284-14249, 2003.

Ting, A. Y. et al., "Genetically Encoded Fluorescent Reporters of Protein Tyrosine Kinase Activities in Living Cells", *PNAS*, 98, No. 26, pp. 15003-15008, 2001.

Violin, J.D. et al., "A Genetically Encoded Fluorescent Reporter Reveals Oscillatory Phosphorylation by Protein Kinase C", *The Journal of Cell Biology*, 161, No. 5, pp. 899-909, 2003.

Wright, D. E. et al., "Fluorometric Assay for Adenosine $3'$,$5'$-Cyclic Menophosphate-Dependent Protein Kinase and Phosphoprotein Phosphatase Activities", *Proceedings of the National Academy of Sciences of the United States of America*, 78, No. 10, pp. 6048-6050, 1981.

Yeh, R. et al., "Real Time Visualization of Protein Kinase Activity in Living Cells", *The Journal of Biological Chemistry*, 277 No. 13, pp. 11527-11532, 2002.

Zhang, J. et al., "Genetically Encoded Reporters of Protein Kinase A Activity Reveal Impact of Substrate Tethering", *PNAS*, 98, No. 26, pp. 14997-15002, 2001.

Shults M.D. et al., "Modular and Tunable Chemosensor Scafford for Divalent Zinc." *J. Am. Chem. Soc.*, 125, pp. 10591-10597, 2003.

International Preliminary Report On Patentability in corresponding PCT Application No. PCT/US2004/032733, dated Apr. 20, 2005, 10 pgs.

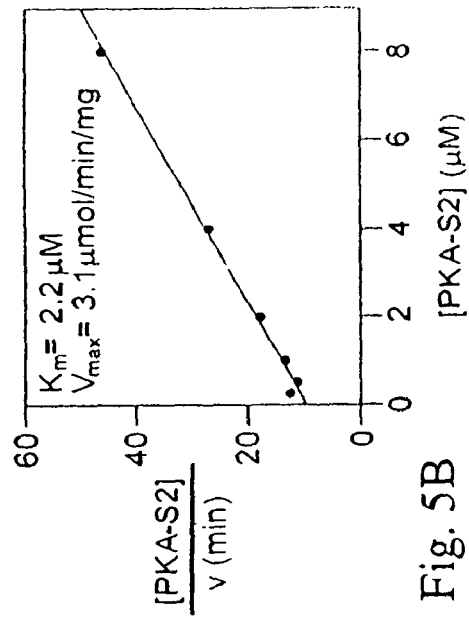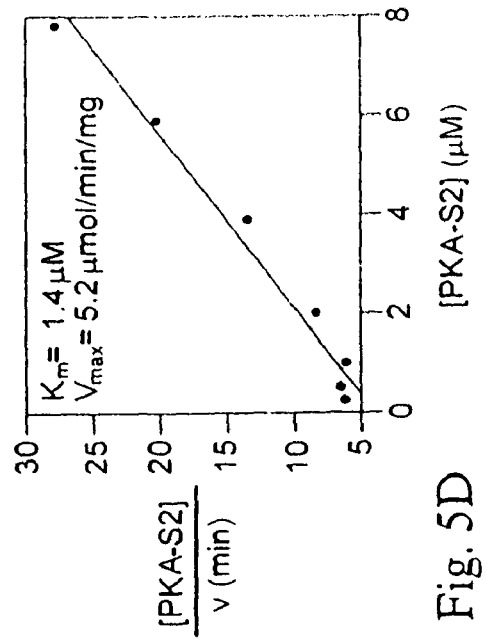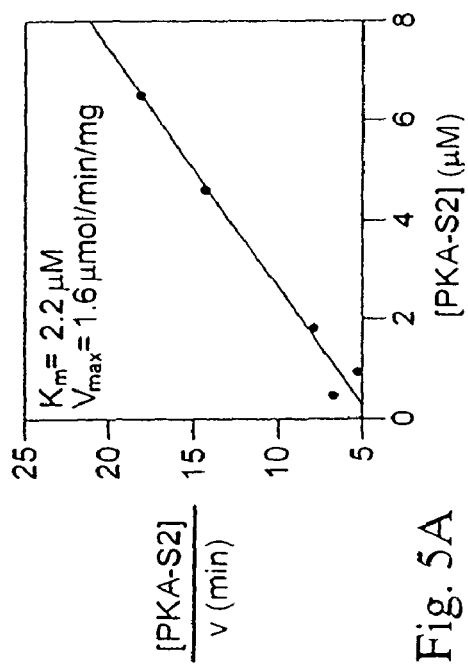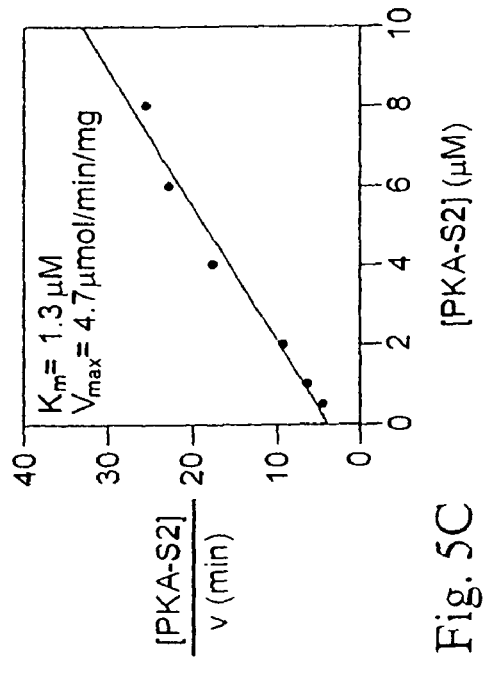
Fig. 5A
Fig. 5B
Fig. 5C
Fig. 5D

SEQUENCE LISTING

```
<160> NUMBER OF SEQ ID NOS: 11

<210> SEQ ID NO 1
<211> LENGTH: 7
<212> TYPE: PRT
<213> ORGANISM: Artificial Sequence
<220> FEATURE:
<223> OTHER INFORMATION: Protein kinase C substrate containing metal
      binding residue (Sox)
<220> FEATURE:
<221> NAME/KEY: MISC_FEATURE
<222> LOCATION: (0)..(1)
<223> OTHER INFORMATION: metal binding amino acid, Sox, of formula (I)
<220> FEATURE:
<221> NAME/KEY: MISC_FEATURE
<222> LOCATION: (3)..(3)
<223> OTHER INFORMATION: phosphorylation site

<400> SEQUENCE: 1

Pro Gly Ser Phe Arg Arg Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Cyclic-AMP dependent kinase (PKA) substrate
      containing metal binding amino acid (Sox)
<220> FEATURE:
<221> NAME/KEY: MISC_FEATURE
<222> LOCATION: (5)..(5)
<223> OTHER INFORMATION: phosphorylation site
<220> FEATURE:
<221> NAME/KEY: MISC_FEATURE
<222> LOCATION: (7)..()
```

```
<223> OTHER INFORMATION: metal binding amino acid, Sox, of formula (I)

<400> SEQUENCE: 2

Leu Arg Arg Ala Ser Leu Pro
1               5

<210> SEQ ID NO 3
<211> LENGTH: 7
<212> TYPE: PRT
<213> ORGANISM: Artificial Sequence
<220> FEATURE:
<223> OTHER INFORMATION: Protein kinase C substrate containing the metal
      binding amino acid (Sox)
<220> FEATURE:
<221> NAME/KEY: MISC_FEATURE
<222> LOCATION: (0)..(1)
<223> OTHER INFORMATION: metal binding amino acid, Sox, of formula (I)
<220> FEATURE:
<221> NAME/KEY: MISC_FEATURE
<222> LOCATION: (3)..(3)
<223> OTHER INFORMATION: phosphorylation site

<400> SEQUENCE: 3

Pro Gly Thr Phe Arg Arg Arg
1               5

<210> SEQ ID NO 4
<211> LENGTH: 12
<212> TYPE: PRT
<213> ORGANISM: Artificial Sequence
<220> FEATURE:
<223> OTHER INFORMATION: Abelson kinase (Abl) substrate containing the
      metal binding amino acid (Sox)
<220> FEATURE:
<221> NAME/KEY: MISC_FEATURE
<222> LOCATION: (0)..(1)
<223> OTHER INFORMATION: metal binding amino acid, Sox, of formula (I)
<220> FEATURE:
<221> NAME/KEY: MISC_FEATURE
<222> LOCATION: (4)..(4)
<223> OTHER INFORMATION: phosphorylation site

<400> SEQUENCE: 4

Pro Gly Ile Tyr Ala Ala Pro Phe Ala Lys Lys Lys
1               5                   10

<210> SEQ ID NO 5
<211> LENGTH: 5
<212> TYPE: PRT
<213> ORGANISM: Artificial Sequence
<220> FEATURE:
<223> OTHER INFORMATION: recognition motif for Protein kinase C (PKC)
<220> FEATURE:
<221> NAME/KEY: MISC_FEATURE
<222> LOCATION: (1)..(1)
<223> OTHER INFORMATION: Xaa is Ser or Thr

<400> SEQUENCE: 5

Xaa Phe Arg Arg Arg
1               5

<210> SEQ ID NO 6
<211> LENGTH: 6
<212> TYPE: PRT
<213> ORGANISM: Artificial Sequence
<220> FEATURE:
<223> OTHER INFORMATION: recognition motif for cyclic-AMP dependent
      kinase (PKA)
<220> FEATURE:
<221> NAME/KEY: MISC_FEATURE
<222> LOCATION: (5)..(5)
```

```
<223> OTHER INFORMATION: Xaa is Ser or Thr

<400> SEQUENCE: 6

Leu Arg Arg Ala Xaa Leu
1               5

<210> SEQ ID NO 7
<211> LENGTH: 6
<212> TYPE: PRT
<213> ORGANISM: Artificial Sequence
<220> FEATURE:
<223> OTHER INFORMATION: recognition motif for Abelson kinase (Abl)

<400> SEQUENCE: 7

Ile Tyr Ala Ala Pro Phe
1               5

<210> SEQ ID NO 8
<211> LENGTH: 4
<212> TYPE: PRT
<213> ORGANISM: Artificial Sequence
<220> FEATURE:
<223> OTHER INFORMATION: sensor
<220> FEATURE:
<221> NAME/KEY: MISC_FEATURE
<222> LOCATION: (1)..(1)
<223> OTHER INFORMATION: Xaa is an amino acid of formula (I)
<220> FEATURE:
<221> NAME/KEY: MISC_FEATURE
<222> LOCATION: (2)..(2)
<223> OTHER INFORMATION: Xaa is independently an amino acid
<220> FEATURE:
<221> NAME/KEY: MISC_FEATURE
<222> LOCATION: (3)..(3)
<223> OTHER INFORMATION: Xaa is independently an amino acid
<220> FEATURE:
<221> NAME/KEY: MISC_FEATURE
<222> LOCATION: (4)..(4)
<223> OTHER INFORMATION: Xaa is a bond or an amino acid residue

<400> SEQUENCE: 8

Xaa Xaa Xaa Xaa
1

<210> SEQ ID NO 9
<211> LENGTH: 5
<212> TYPE: PRT
<213> ORGANISM: Artificial Sequence
<220> FEATURE:
<223> OTHER INFORMATION: sensor
<220> FEATURE:
<221> NAME/KEY: MISC_FEATURE
<222> LOCATION: (1)..(1)
<223> OTHER INFORMATION: Xaa is an amino acid of formula (I)
<220> FEATURE:
<221> NAME/KEY: MISC_FEATURE
<222> LOCATION: (2)..(2)
<223> OTHER INFORMATION: Xaa is independently an amino acid
<220> FEATURE:
<221> NAME/KEY: MISC_FEATURE
<222> LOCATION: (3)..(3)
<223> OTHER INFORMATION: Xaa is independently an amino acid
<220> FEATURE:
<221> NAME/KEY: MISC_FEATURE
<222> LOCATION: (4)..(4)
<223> OTHER INFORMATION: Xaa is a bond or an amino acid residue
<220> FEATURE:
```

```
<221> NAME/KEY: MISC_FEATURE
<222> LOCATION: (5)..(5)
<223> OTHER INFORMATION: Xaa is a hydroxyl containing amino acid

<400> SEQUENCE: 9

Xaa Xaa Xaa Xaa Xaa
1               5

<210> SEQ ID NO 10
<211> LENGTH: 3
<212> TYPE: PRT
<213> ORGANISM: Artificial Sequence
<220> FEATURE:
<223> OTHER INFORMATION: sensor
<220> FEATURE:
<221> NAME/KEY: MISC_FEATURE
<222> LOCATION: (1)..(1)
<223> OTHER INFORMATION: Xaa is an independently amino acid
<220> FEATURE:
<221> NAME/KEY: MISC_FEATURE
<222> LOCATION: (2)..(2)
<223> OTHER INFORMATION: Xaa is an independently an amino acid
<220> FEATURE:
<221> NAME/KEY: MISC_FEATURE
<222> LOCATION: (3)..(3)
<223> OTHER INFORMATION: Xaa is an amino acid of formula (I)

<400> SEQUENCE: 10

Xaa Xaa Xaa
1

<210> SEQ ID NO 11
<211> LENGTH: 5
<212> TYPE: PRT
<213> ORGANISM: Artificial Sequence
<220> FEATURE:
<223> OTHER INFORMATION: sensor
<220> FEATURE:
<221> NAME/KEY: MISC_FEATURE
<222> LOCATION: (1)..(1)
<223> OTHER INFORMATION: Xaa is a hydroxyl containing amino acid
<220> FEATURE:
<221> NAME/KEY: MISC_FEATURE
<222> LOCATION: (2)..(2)
<223> OTHER INFORMATION: Xaa is a bond or an amino acid residue
<220> FEATURE:
<221> NAME/KEY: MISC_FEATURE
<222> LOCATION: (3)..(3)
<223> OTHER INFORMATION: Xaa is an independently an amino acid
<220> FEATURE:
<221> NAME/KEY: MISC_FEATURE
<222> LOCATION: (4)..(4)
<223> OTHER INFORMATION: Xaa is an independently an amino acid
<220> FEATURE:
<221> NAME/KEY: MISC_FEATURE
<222> LOCATION: (5)..(5)
<223> OTHER INFORMATION: Xaa is an amino acid of formula (I)

<400> SEQUENCE: 11

Xaa Xaa Xaa Xaa Xaa
1               5
```

FLUORESCENCE ASSAY FOR KINASE ACTIVITY

RELATED APPLICATIONS

The present application is a divisional of U.S. patent application Ser. No. 10/819,587, filed Apr. 6, 2004 now U.S. Pat. No. 7,262,282, which is a continuation-in-part of U.S. patent application Ser. No. 10/681,427, filed Oct. 8, 2003, now U.S. Pat. No. 6,906,194.

FEDERALLY SPONSORED RESEARCH OR DEVELOPMENT

The subject matter of this application was developed in part with funding from the National Institute of Health (grant application no. GM64346). The government may have certain rights in this technology.

BACKGROUND

The present invention provides sensors to monitor protein kinase activity continuously with a fluorescence readout. The sensor requires minimal perturbation of a protein kinase peptide substrate. The fluorescence response with respect to time over the course of the reaction corresponds to enzyme activity. The sensor of the present invention can be used in high-throughput screening of inhibitors or substrates, detection of activity in cell extracts or enzyme purifications, spatial or temporal localization of kinase activity in a cell, and elucidation of complicated signal transduction pathways.

Protein kinases are involved in all aspects of regulation within cells. A protein kinase catalyzes the transfer of a phosphate group from adenosine triphosphate (ATP) to a serine, threonine or tyrosine residue in a peptide or protein sequence. Each kinase is specific for the amino acids surrounding the residue to be phosphorylated. The traditional method for assaying kinase activity is discontinuous and requires 32P-labelled ATP, which requires special handling. Many companies market specialized fluorescence kinase assay systems, all of which are discontinuous, requiring sampling of the reaction mixture followed by additional handling steps to label the product of the reaction with a fluorescent moiety (e.g., Promega, Panvera, Calbiochem, Cell Signaling Technology, Molecular Devices, DiscoveRx, Upstate, PerkinElmer). A continuous fluorescence assay that can be performed in real time is of great utility. Currently, few examples of sensors capable of such assays exist.

Approaches include: environment-sensitive fluorophores near the phosphorylation site (Wright, D. E. et al. Proc. Natl. Acad. Sci. USA 1981, 78, 6048-6050; McIlroy, B. K. et al. Anal. Biochem. 1991, 195, 148-152; Higashi, H. et al. FEBS Lett. 1997, 414, 55-60; Post, P. I. et al. J. Biol. Chem. 1994, 269, 12880-12887), FRET pairs flanking a sequence which undergoes a conformational change upon phosphorylation (Nagai, Y. et al. Nat. Biotech. 2000, 18, 313-316; Ohuchi, Y. et al. Analyst 2000, 125, 1905-1907; Zhang, J. et al. Proc. Natl. Acad. Sci. USA 2001, 98, 14997-15002; Ting, A. Y. et al. Proc. Natl. Acad. Sci. USA 2001, 98, 15003-15008; Hofmann, R. M. et al. Bioorg. Med. Chem. Lett. 2001, 11, 3091-3094; Kurokawa, K. at el. J. Biol. Chem. 2001, 276, 31305-31310; Sato, M. et al. Nat. Biotech. 2002, 20, 287-294; Violin, J. D. et al. J. Cell Biol. 2003, 161, 899-909), or $Ca^{2+}$ chelation between the phosphate and in internal chelator causing disruption of PET-quenching (Chen, C.-A.; et al. J. Am. Chem. Soc. 2002, 124, 3840-3841). A majority of these sensors have very modest fluorescence increases or sometimes decreases, with the notable exception of 1.5-2.5-fold increases in the probes reported by Lawrence and coworkers (Chen 2002, supra; Yeh, R.-H.; et al. J. Biol. Chem. 2002, 277, 11527-11532). However, these types of probes, with fluorophores adjacent to the phosphorylated residue or very large fluorophores may interfere with their recognition by and reactivity with certain kinases.

BRIEF SUMMARY

The present invention provides novel metal binding amino acid residues of the formula (I) which exhibit chelation-enhanced fluorescence (CHEF) upon binding to $Mg^{2+}$. One especially preferred amino acid residue (III) referred to as "Sox" is disclosed.

The present invention also provides peptides which include the metal binding amino acid residues (I) of the present invention.

The present invention also provides peptidyl sensors which include the metal binding amino acid residues (I). These sensors also contain a kinase recognition sequence with a hydroxyl amino acid that can be phosphorylated in the presence of a kinase. The metal binding amino acid residue (I) is located on either side (N-terminally or C-terminally) of the hydro-oxyl amino acid and is preferably separated from that recognition sequence by a peptide which is capable of assuming a β-turn conformation ("a β-turn sequence"). In some cases, the β-turn sequence is separated from the hydroxyl amino acid by another amino acid.

BRIEF DESCRIPTION OF THE FIGURES

FIG. 1 depicts two designs of sensors according to the present invention.

FIG. 5 are Hanes plots of Ac-Leu-Arg-Arg-Ala-Ser-Leu-Pro-Sox-NH$_2$ (SID No: 2) reaction with PKA.

DETAILED DESCRIPTION OF THE INVENTION

The present invention provides a sensor for the detecting of kinase activity within peptides containing kinase recognition motifs.

Figure 1A:
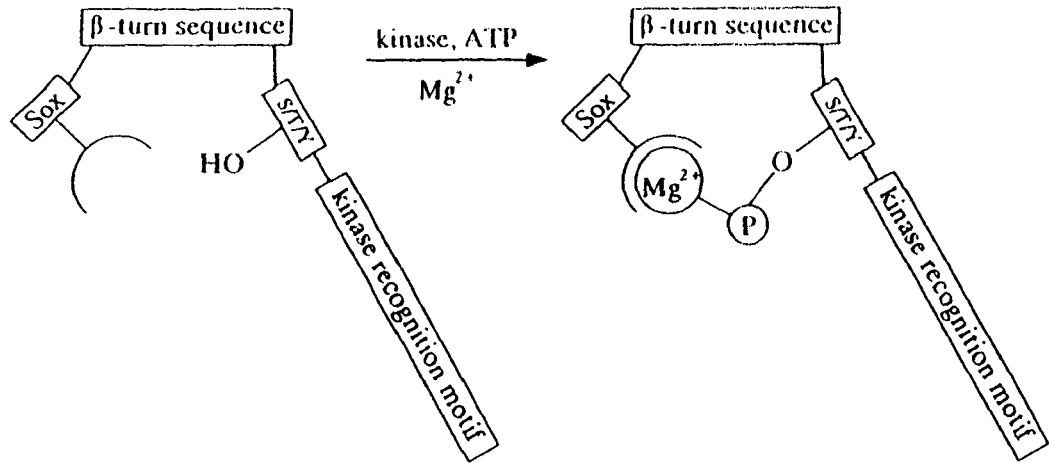
In FIG. 1A, the metal binding amino acid is N-terminal to the phosphorylation site.
Figure 1B:
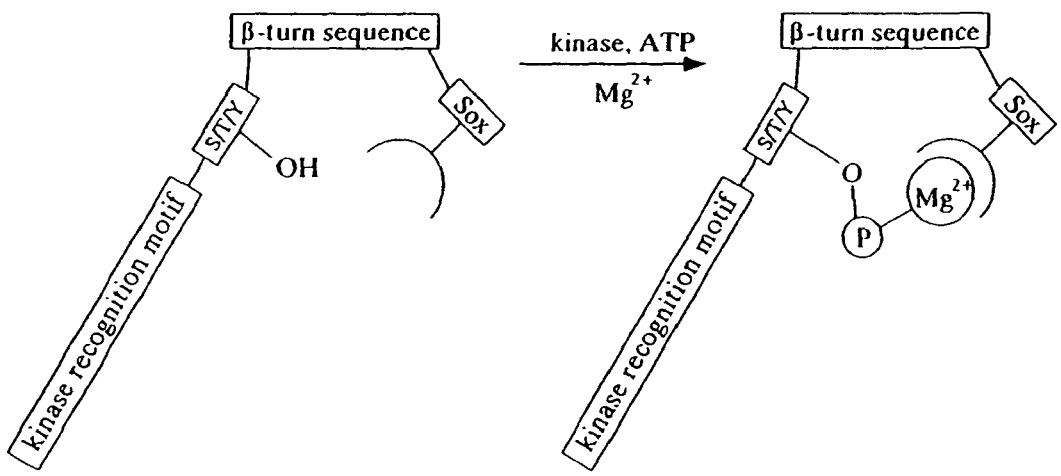
In FIG. 1B, the metal binding amino acid is C-terminal to the phosphorylation site.
Figure 2A:
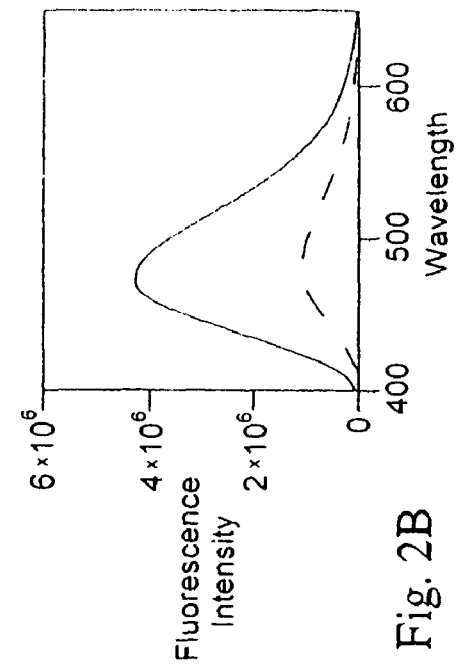
FIG. 2 are graphs depicting the fluorescence spectra of 10 µM each of phosphorylated (solid line) and unphosphorylated (dashed line) peptides in the appropriate assay mixture without enzyme: (a) Ac-Sox-Pro-Gly-(p)Ser-Phe-Arg-Arg-Arg-NH$_2$ (SID No: 1); (b) Ac-Leu-Arg-Arg-Ala-(p)Ser-Leu-Pro-Sox-NH$_2$ (SID No:2); (c) Ac-Sox-Pro-Gly-(p)Thr-Phe-Arg-Arg-Arg-NH$_2$ (SID No:3); and (d) Ac-Sox-Pro-Gly-Ile-(p)Tyr-Ala-Ala-Pro-Phe-Ala-Lys-Lys-Lys-NH$_2$ (SID No:4).
Figure 2B:
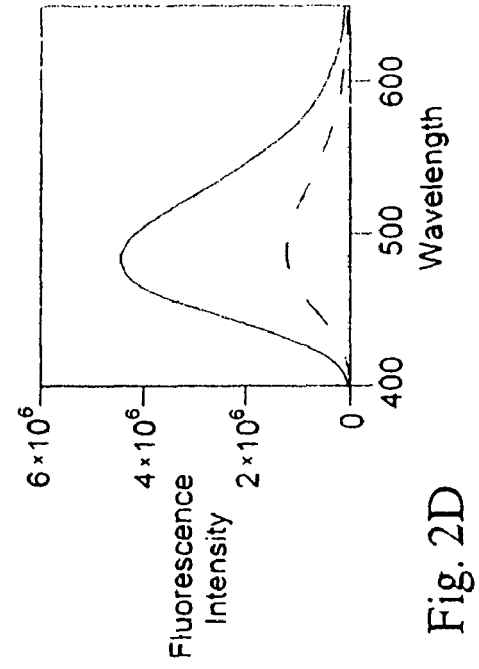
Figure 2C:
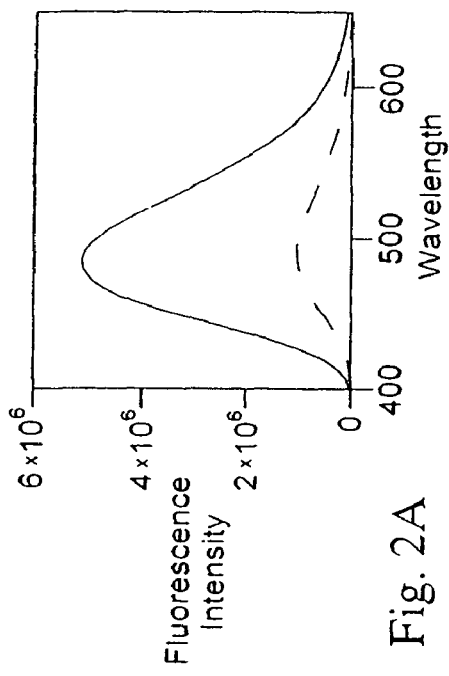
Figure 2D:
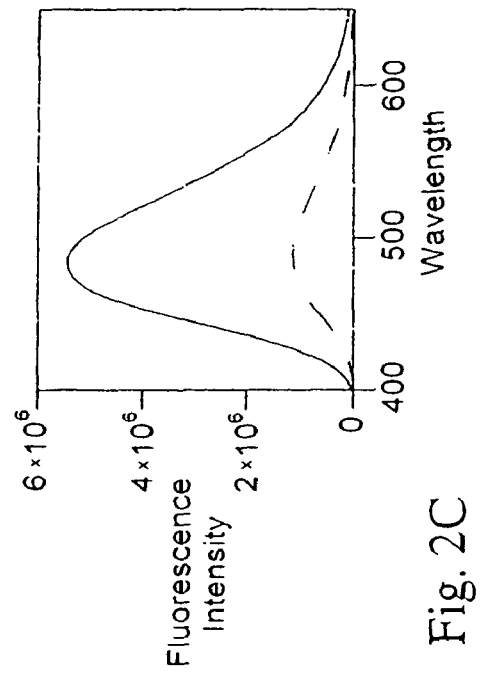

Sensors in accordance with the present invention are illustrated in FIG. 1. The sensor comprises a metal binding amino acid, a phosphorylation site within a kinase recognition motif, a β-turn sequence, and $Mg^{2+}$ present in the medium.

The metal binding amino acid is of the formula (I)

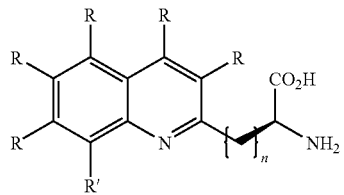

where at least one R group is —SO₂X, where X is —OR" or —NR"R'";
R' is hydroxy, amino, or thiol;
R" is $C_{1-6}$ alkyl;
R'" is hydrogen or alkyl; and
n is 1, 2 or 3.

In another preferred embodiment, the metal binding amino acid is of the formula (III):

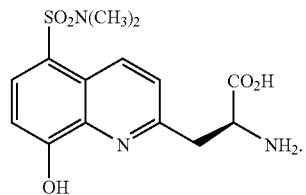

Residue (III) is referred to herein as Sox. The kinetic and fluorescence properties of various protein kinase substrates containing Sox in various kinase recognition motifs is shown below in Table I.

TABLE I

| Target Kinase | Substrate Sequence[a] | KM (μM)[b] | Vmax (μmol/min/mg)[b] | Fluorescence Increase[c] |
|---|---|---|---|---|
| PKC | Ac-Sox-PGS*FRRR-NH₂ (SID No: 1) | 8.6 ± 2.9[d] | 5.9 ± 1.9[d] | 470%[e] |
| PKA | Ac-LRRAS*LP-Sox-NH₂ (SID No: 2) | 1.8 ± 0.5[f] | 3.7 ± 1.6[f] | 300%[e] |
| PKC | Ac-Sox-PGT*FRRR-NH₂ (SID No: 3) | 23 ± 3[d] | 2.3 ± 0.6[d] | 280%[g] |
| Abl | Ac-Sox-PGIY*AAPFAKKK-NH₂ (SID No: 4) | — | — | 400%[g] |

[a]Residue that is phosphorylated is marked with an asterisk (*).
[b]$K_m$ and $V_{max}$ values were obtained from initial slopes of reaction assays, corrected appropriately for substrate and product fluorescence. Reported values are an average of four values from separate Hanes plots.
[c]Excitation wavelength: 360 nm, Emission wavelength, 485 nm.
[d]Assay conditions: 20 mM HEPES, pH 7.4, 10 mM MgCl₂, 0.3 mM CaCl₂, 1 mM ATP, 1 mM DTT, 0.5 μg/ml phosphatidylserine, 0.1 μg/ml diacylglycerol, 0.7 nM PKC_a 30° C.
[e]Calculated from slope (units/μM) of product and substrate concentration versus fluorescence intensity.
[f]Assay conditions: 20 mM HEPES, pH 7.4, 10 mM MgCl₂, 1 mM ATP, 1 mM DTT, 40 units PKA, 30° C.
[g]Calculated from single peptide solutions (10 μM).

The metal binding amino acids of the present invention undergo chelation-enhanced fluorescence (CHEF) upon binding to $Mg^{2+}$. The florescence of amino acid residues in accordance with the present invention increase by at least about 100%, preferably by at least about 200%, more preferably by at least about 300%, when bound to $Mg^{2+}$.

In a preferred embodiment, the metal binding amino acid is of the formula (II):

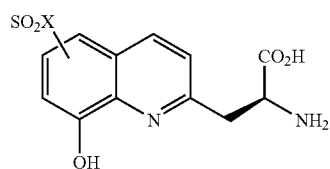

where X is —OR" or —NR"R'"; R" is $C_{1-6}$ alkyl; and R'" is hydrogen or $C_{1-6}$ alkyl. Preferably X is located in the 5-position on the ring system. Preferably X is —NR"R'". Preferably both R" and R'" are both $C_{1-6}$ alkyl.

The capping group is of the formula (IV):

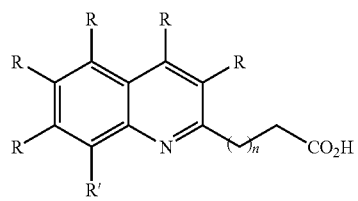

where at least one R group is —SO₂X, where X is —OR" or —NR"R'"; R' is hydroxy, amino, or thiol; R" is $C_{1-6}$ alkyl; R'" is hydrogen or $C_{1-6}$ alkyl; and n=0, 1, 2, or 3. The capping group (IV) bonds to the N-terminus of a peptide and thus serves as an amino protecting group.

In one embodiment the N-terminus of a peptide is protected with the capping group of the formula (IV).

Phosphorylation sites in accordance with the present invention include hydroxyl-containing amino acids within kinase recognition motifs. Examples include naturally occurring hydroxyl-containing amino acid residues, such as serine, threonine and tyrosine, and non-naturally occurring hydroxyl-containing amino acid residues.

Any kinase recognition motif known in the art can be used in accordance with the present invention. Recognition sequences with acidic residues may show a lessor magnitude of fluorescence increase upon phosphorylation than comparable sequences, as the affinity of the unphosphorylated peptide for $Mg^{2+}$ increases under acidic conditions. Examples of recognition motifs which can be monitored for phosphorylation using the metal binding amino acids of the present invention are shown in Table II:

TABLE II

| Kinase | recognition motif |
|---|---|
| Protein kinase C (PKC) | -Ser/Thr-Phe-Arg-Arg-Arg- (SID No: 5) |
| cyclic-AMP dependent kinase (PKA) | -Leu-Arg-Arg-Ala-Ser/Thr-Leu- (SID No: 6) |
| Abelson kinase (Abl) | -Ile-Tyr-Ala-Ala-Pro-Phe (SID No: 7) |

A list of other peptides which can be phosphorylated (and the corresponding kinases) is found in Table I of Pinna & Donella-Deana, Biochemica et Biophysica Acta 1222: 415-431 (1994); incorporated herein by reference in its entirety. Another list can be found at online at www.neb.com/neb/tech/tech_resource/protein_tools/substraye_recognition.html (a copy of this website as it existed on Sep. 26, 2003 is provided in an information disclosure statement submitted concurrently with this application; and is incorporated by reference in its entirety).

The hydroxyl amino acid is separated from the metal binding amino acid residue (I) of the present invention by a dipeptidyl β-turn sequence. In addition to this β-turn sequence, another amino acid may also separate the hydroxyl amino acid from the metal binding amino acid residue (1). For probes of tyrosine kinase activity, this additional amino acid is typically included in the sensor adjacent to the β-turn sequence to accommodate the larger tyrosine side chain.

Any β-turn sequence known in the art can also be used in accordance with the present invention. Both L-amino acids and D-amino acids can be part of the β-turn sequence. Preferably, when the metal binding amino acid is located C-terminally to the phosphorylation site, the β-turn sequence is Pro-Gly. Preferably, when the metal binding amino acid is located N-terminally to the phosphorylation site, the β-turn sequence is Gly-Pro. Gly may be replaced with certain other amino acids to include an additional binding determinant in the sequence.

In one embodiment, the sensor comprises a sequence (SID No. 8):

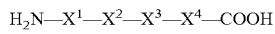
$H_2N—X^1—X^2—X^3—X^4—COOH$ where $X^1$ is an amino acid of the formula (I); $X^2$ and $X^3$ are each, independently, amino acid residues which together form a β-turn sequence; and $X^4$ is a bond or an amino acid residue. In this embodiment, $X^1$ is preferably Sox, $X^2$ is Pro, and $X^3$ is Gly.

In another embodiment, the sensor comprises a sequence (SID No. 9):

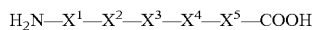
$H_2N—X^1—X^2—X^3—X^4—X^5—COOH$ where $X^1$ is an amino acid of the formula (I); $X^2$ and $X^3$ are each, independently, amino acid residues which together form a β-turn sequence; $X^4$ is a bond or an amino acid residue; $X^5$ is a hydroxyl containing amino acid. In this embodiment, $X^5$ is preferably the hydroxyl residue in a kinase recognition motif, and the remainder of the kinase recognition motif is attached to $X^5$.

In another embodiment, the sensor comprises the sequence (SID No. 10):

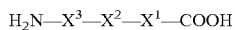
$H_2N—X^3—X^2—X^1—COOH$ where $X^1$ is an amino acid of the formula (I); and $X^2$ and $X^3$ are each, independently, amino acids which together form a β-turn sequence. In this embodiment, $X^1$ is preferably Sox, $X^2$ is Leu, and $X^3$ is Pro.

In another embodiment, the sensor comprises a sequence (SID No. 11):

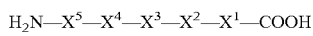
$H_2N—X^5—X^4—X^3—X^2—X^1—COOH$ where $X^1$ is an amino acid of the formula (I); $X^2$ and $X^3$ are each, independently, amino acids which together form a β-turn sequence; $X^4$ is a bond or an amino acid residue; and $X^5$ is a hydroxyl containing amino acid. In this embodiment, $X^5$ is preferably the hydroxyl residue in a kinase recognition motif, and the remainder of the kinase recognition motif is attached to $X^5$.

The sensor of the present invention can be used in a method for detecting kinase activity. The method of the present invention comprises providing a sensor comprising a kinase recognition motif containing a phosphorylation site, and a metal binding amino acid of the formula (I) near to a β-turn sequence; contacting the sensor with a sample comprising $Mg^{2+}$, a phosphate source, and a kinase; and analyzing for the presence of a phosphorylated peptide product.

The method of the present invention can be used in vitro or in vivo. For in vitro applications, the reaction is typically conducted in a buffer containing $Mg^{2+}$ and a phosphate source. Suitable buffers include HEPES and TRIS. A preferred $Mg^{2+}$ source is $MgCl_2$. A preferred phosphate source is ATP.

Serine/threonine and tyrosine kinases can be used in the present invention. Exemplary kinases include cAMP dependent protein kinase, protein kinase C, Ca/calmodulin dependent kinases, AMP activated kinase, s6 kinases, eIF-2 kinases, p34$^{cdc2}$ protein kinase, mitogen activated protein kinases, casein kinase-2, casein kinase-1, glycogen sythase kinase-3, Tyr-specific protein kinases.

For in vitro applications, the concentration of kinase can range from about 0.5 nM to about 1 μM, typically not more than about 500 nM, and preferably not more than about 250 nM. The concentrations of sensor can vary, but is usually ranges between about 0.1 μM to 10 mM. Adenosine 5'-triphosphate (ATP) is the preferred source of phosphate, in stock solutions of about 10-100 mM. Because most kinases have $K_m$ values for ATP in the range of about 10-150 μM, saturating concentrations of ATP are used to arrive at values of $K_m$ and $V_{max}$ for the substrates.

For in vivo applications, when the sensor is internalized into a cell, sufficient kinases, $Mg^{2+}$ and phosphate sources exist in the cytosol. For in vivo sensing, a cellular internalization sequence can be included in the sensor design. Suitable cellular internalization sequences include Penetratins, HIV-Tat domains and poly-arginine sequences (Lindgren, M. et al. Trends Pharamol. Sci. 2000, 21, 99-103; Wadia, J. S. et al. Curr Opin. Biotech. 2002, 13, 52-56).

For applications in which the kinase is dependent on cofactors, a source of cofactor is also included in the sample. For example, for PKC, sources of $Ca^{2+}$, phospholipid and diacylglycerol are needed.

The sensor of the present invention can be used to measure a kinase reaction continuously, as the metal binding amino acid residue (I) does not experience photobleaching.

It is therefore intended that the foregoing detailed description be regarded as illustrative rather than limiting, and that it be understood that it is the following claims, including all equivalents, that are intended to define the spirit and scope of this invention.

EXAMPLES

Peptide Synthesis

Peptides were synthesized using standard Fmoc amino acid protection chemistry on Fmoc-PAL-PEG-PS resin (0.22 mmol equiv.). Couplings of Fmoc-protected amino acids to the resin were carried out with 1-benzotriazolyoxytris(pyrrolidino) phosphonium hexafluorophosphate (PyBOP), 1-hydroxybenzotriazole (HOBt) and diisopropylethylamine (DIEA) or O-(7-azabenzotrazol-1-yl)-1,1,3,3-tetramethyl uranium hexafluorophosphate (HATU) and DIEA to generate the activated ester. The resin was swelled in dichloromethane (5 min.) then DMF (5 min.) prior to synthesis. All amino acids other than the Sox, phosphoserine, phosphothreonine and phosphotyrosine were added by the following representative procedure: removal of the Fmoc group (20% piperidine solution in DMF, 3×5 min.), wash (DMF, 5×1 min.), coupling (amino acid/PyBOP/DIEA, 6:6:6, 0.05 M in DMF, 45 min.), rinse (DMF, 2×1 min; DCM, 2×1 min.). To couple the Sox residue, double coupling with 2 equivalents each time was used (Fmoc-Sox-OH/PyBOP/DIEA, 2:2:2, 0.15M in DMF, 2×120 min.). To couple the phosphoamino acid residues, HATU was used (Fmoc-Xaa(PO(OBzl)OH)—OH/HATU/DIEA, 3:3:3, 0.05 M in DMF, 30 min.).

After addition of the final residue, the peptide was acetyl-capped (pyridine/acetic anhydride, 20:20, 0.15 M in DMF, 30 min.), and a final deblock cycle (20% piperidine in DMF, 3×5 min.) was performed to cleave any Sox aryl ester formed. The resin was dried under high vacuum overnight prior to a 2.5-hour cleavage with trifluoroacetic acid/triisopropylsilane/water (95:2.5:2.5, 40 ml/mg resin for unphosphorylated peptides and 140 ml/mg resin for phosphorylated peptides).

The resulting solution was concentrated under a stream of nitrogen, and the peptide precipitated by addition of cold 1:1 diethyl ether:hexanes solution. The pellet was triturated with cold 1:1 ether:hexanes (3×1.5 ml for 15 mg resin), redissolved in water, filtered and lyophilized overnight. Peptides were purified by preparatory reverse-phase HPLC ($C_{18}$), and only fractions containing a single peak by analytical HPLC ($C_{18}$) with the correct mass (ES-MS) were used for analytical experiments.

TABLE III

Characterization Data for Peptides

| Kinase | Sequence | HPLC Ret. Time (min) | $[M + H]^+$ Calcd | $[M + H]^+$ found[c] |
|---|---|---|---|---|
| PKC | Ac-Sox-Pro-Gly-Ser-Phe-Arg-Arg-Arg-$NH_2$ (SID No: 1) | 26.7[a] | 413.2 (+3) | 413.2 |
| | Ac-Sox-Pro-Gly-pSer-Phe-Arg-Arg-Arg-$NH_2$ (SID No: 1) | 25.7[a] | 659.3 (+2) | 659.2 |
| | Ac-Sox-Pro-Gly-Thr-Phe-Arg-Arg-Arg-$NH_2$ (SID No: 3) | 22.8[b] | 417.9 (+3) | 417.9 |
| | Ac-Sox-Pro-Gly-pThr-Phe-Arg-Arg-Arg-$NH_2$ (SID No: 3) | 21.6[b] | 666.3 (+2) | 666.3 |
| PKA | Ac-Leu-Arg-Arg-Ala-Ser-Leu-Pro-Sox-$NH_2$ (SID No: 2) | 25.9[b] | 587.8 (+2) | 576.8 |
| | Ac-Leu-Arg-Arg-Ala-pSer-Leu-Pro-Sox-$NH_2$ (SID No: 2) | 25.1[b] | 627.9 (+2) | 627.8 |
| Abl | Ac-Sox-Pro-Gly-Ile-Tyr-Ala-Ala-Pro-Phe-Ala-Lys-Lys-Lys-$NH_2$ (SID No: 4) | 21.1[c] | 551.6 (+3) | 552.0 |
| | Ac-Sox-Pro-Gly-Ile-pTyr-Ala-Ala-Pro-Phe-Ala-Lys-Lys-Lys-$NH_2$ (SID No: 4) | 20.1[c] | 578.3 (+3) | 578.3 |

[a]$C_{18}$; solvent A = water, 0.1% v/v TFA; solvent B = MeCN, 0.1% v/v TFA, 5 min. 7% B followed by linear gradient 10-50% B over 30 min.
[b]$C_{18}$; solvent A = water, 0.1% v/v TFA; solvent B = MeCN, 0.1% v/v TFA, 5 min. 10% B followed by linear gradient 15-50% B over 30 min.
[c]$C_{18}$; solvent A = water, 0.1% v/v TFA; solvent B = MeCN, 0.1% v/v TFA, 5 min. 10% B followed by linear gradient 20-70% B over 30 min.
[d]ES-MS data was collected on a PE Biosystems Mariner mass spectrometer.

Stock Solutions:

Due to the affinity of the phosphorylated peptides for $Zn^{2+}$, the reagents with the highest purity and lowest metal content were used to avoid the necessity of removing metal ion impurities after preparations.

The following solutions were prepared prior to the day of the assay and stored at room temperature unless otherwise indicated:

1) Stock solution of the peptides were prepared in ultrapure (18 MΩ) water and their concentrations were determined by UV/VIS (based on the determined extinction coefficient of the fluorophore unit, 5-(N,N-dimethylsulfonamido)-8-hydroxy-2-methylquinoline, ε=8247 M−1 cm−1 at 355 nm in 0.1 M NaOH with 1 mM $Na_2$EDTA). An average of the values from four separate solutions, each prepared using a different volume of the stock solution, was read on a Beckman DU 7500 Spectrophotometer. Peptide stock solutions were stored at 4° C.

2) Magnesium chloride stock solution of about 3 M and calcium chloride stock solution of about 0.3 M were prepared from Alfa Aesar's Puratronic grade salts. Most commercially available salts contain $Zn^{2+}$ as significant impurities (Thompson, R. B. et al. J. Neurosci. Methods 2000, 96, 35-45) and should not be used due to the high affinity of the phosphorylated peptides for $Zn^{2+}$. The $Mg^{2+}$ and $Ca^{2+}$ concentrations were determined by titration with a standardized solution of EDTA (Aldrich) in the presence of an Eriochrome Black T (Aldrich) (Basset, J. et al. Vogel's Textbook of Quantitative Inorganic Analysis; William Clowers: London, 1978).

3) 20 mM HEPES pH 7.4 was prepared from HEPES (SigmaUltra) adjusted to pH 7.4 with sodium hydroxide (99.998+%, Aldrich) solution (1 M).

4) 20 mM HEPES pH 7.4 containing 12.5 mM $MgCl_2$ and 0.38 mM $CaCl_2$ was prepared by addition of small volumes of stock solutions of $MgCl_2$ and $CaCl_2$ to solution 3.

5) 20 mM HEPES pH 7.4 containing 12.5 mM $MgCl_2$ was prepared in an analogous way to solution 4.

6) 20 mM HEPES pH 7.4 with 5 mM dithiothreitol was prepared by first degassing solution 3 and then adding it to dithiothreitol (Biotechnology grade, Mallinckrodt). The solution was stored at −80° C.

7) 100 mM ATP was prepared with adenosine 5'-triphosphate (Disodium salt, Low Metals Grade, Calbiochem) dissolved in ultrapure (18 MΩ) water and the solution was stored at −80° C.

8) 10 μg/ml phosphatidylserine and 2 μg/ml diacylglycerol in 20 mM HEPES pH 7.4 was prepared by combination of appropriate volumes of chloroform solutions of 10 mg/ml porcine brain phosphatidylserine (Avanti Polar Lipids, Inc.) and 2 mg/ml 1,2-dioleoyl-sn-glycerol (Avanti Polar Lipids, Inc.). The chloroform was evaporated and solution 3 was added. The solution was alternated between vortexing for 3 min. intervals and incubating in a warm water bath for 1 min. for a total time of 12 min. The solution was stored at −20° C.

Assay Recipes:

PKC: On the day of the assay, a 1 μl aliquot of Protein Kinase $C_\alpha$ (Human, Recombinant, Calbiochem) was diluted with 20 μl of solution 4 and stored on ice. A typical reaction contained solution 4 (84 μl), solution 6 (19 μl), solution 8 (5 μl), solution 7 (1 μl), and enzyme working stock (1 μl). An appropriate volume of substrate stock solution was added to begin the reaction.

PKA: On the day of the assay, a 1 μl aliquot of cAMP-dependent Protein Kinase (Catalytic Subunit, Mouse, Recombinant, Calbiochem) was diluted with 80 μl of 50 mM TRIS pH 7.5 containing 10 mM $MgCl_2$ and 0.3 mg/ml BSA and maintained on ice. A typical reaction contained solution 5 (90 μl), solution 6 (20 μl), solution 7 (1 μl) and an appropriate volume of substrate stock solution. Enzyme working stock (1 μl) was added to begin the reaction.

Fluorescence Experiments:

Fluorescence experiments were performed on a Fluoromax 3 from Jobin Yvon. 5 nm emission and excitation slit widths were used. For all experiments, an excitation wavelength of 360 nm was used. Enzyme assays were performed by monitoring emission at 485 nm.

Spectral Comparison of Phosphorylated and Unphosphorylated Peptides:

FIG. 2 depicts the fluorescence spectra of 10 μM each of phosphorylated (solid line) and unphosphorylated (dashed line) peptides in the appropriate assay mixture without enzyme: (a) Ac-Sox-Pro-Gly-(p)Ser-Phe-Arg-Arg-Arg-$NH_2$ (SID No:1) (b) Ac-Leu-Arg-Arg-Ala-(p)Ser-Leu-Pro-Sox-$NH_2$ (SID No:2) (c) Ac-Sox-Pro-Gly-(p)Thr-Phe-Arg-Arg-Arg-$NH_2$ (SID No:3) (d) Ac-Sox-Pro-Gly-Ile-(p)Tyr-Ala-Ala-Pro-Phe-Ala-Lys-Lys-Lys-$NH_2$ (SID No:4). All peptides have a maximum fluorescence emission at 485 nm, with the exception of Ac-Leu-Arg-Arg-Ala-pSer-Leu-Pro-Sox-$NH_2$ (SID No:2), which has a maximum emission wavelength at 474 nm. Though this is likely indicative of a complex forming other than a 1:1 complex, the maximum emission wavelength is constant over a wide range of peptide concentrations with 10 mM $MgCl_2$.

Determination of Kinetic Constants from Fluorescence Data

To solve for $K_m$ and $V_{max}$ for this reaction, determination of the initial rate of product formation from the increase in fluorescence intensity is necessary. With this sensor, a correction for the decrease in fluorescence intensity due to the starting material being consumed is needed to determine the rate of product formation from the initial slope. The fluorescence intensity at any given point can be determined from the following equation:

$$I(t) = f_S S(t) + f_P P(t) \tag{1}$$

where I(t) is the fluorescence intensity, S(t) is the amount of substrate in μM, P(t) is the amount of product in μM, $f_S$ is the fluorescence intensity per μM of substrate, and $f_P$ is fluorescence intensity per μM of product. The amount of substrate and product at any given point are related by:

$$S(t) + P(t) = S_0 \tag{2}$$

where $S_0$ is the initial amount of substrate. Substitution of (2) into (I) followed by rearrangement, yields:

$$P(t) = \frac{I(t) - f_S S_0}{f_P - f_S} \tag{3}$$

The initial velocity of the reaction is the change in the amount of product over time, so taking the derivative of (3) with respect to time gives:

$$v = \frac{dP(t)}{dt} = \frac{\frac{dI(t)}{dt}}{f_P - f_S} \tag{4}$$

The initial slope of the reaction, dI(t)/dt, was measured within the first 5% of substrate turnover. The constants $f_P$ and $f_S$ were calculated from the slope of a line of fluorescence intensity versus concentration of P and S, respectively. A linear fit of a Hanes plot ([S]/V vs. V) was used to find $K_m$ and $V_{max}$.

Figure 3A:
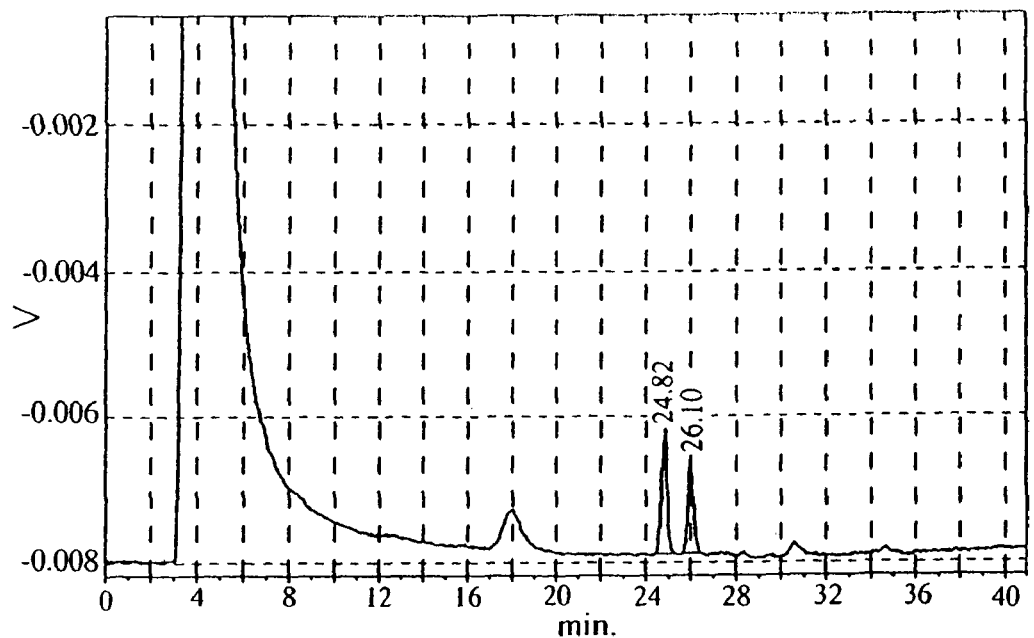
FIG. 3A is an high performance liquid chromatography (HPLC) trace of the reaction of Ac-Leu-Arg-Arg-Ala-Ser-Leu-Pro-Sox-NH$_2$ (SID No:2) (7.8 µM) by PKA after 18 min. at 30° C.
Figure 3B:
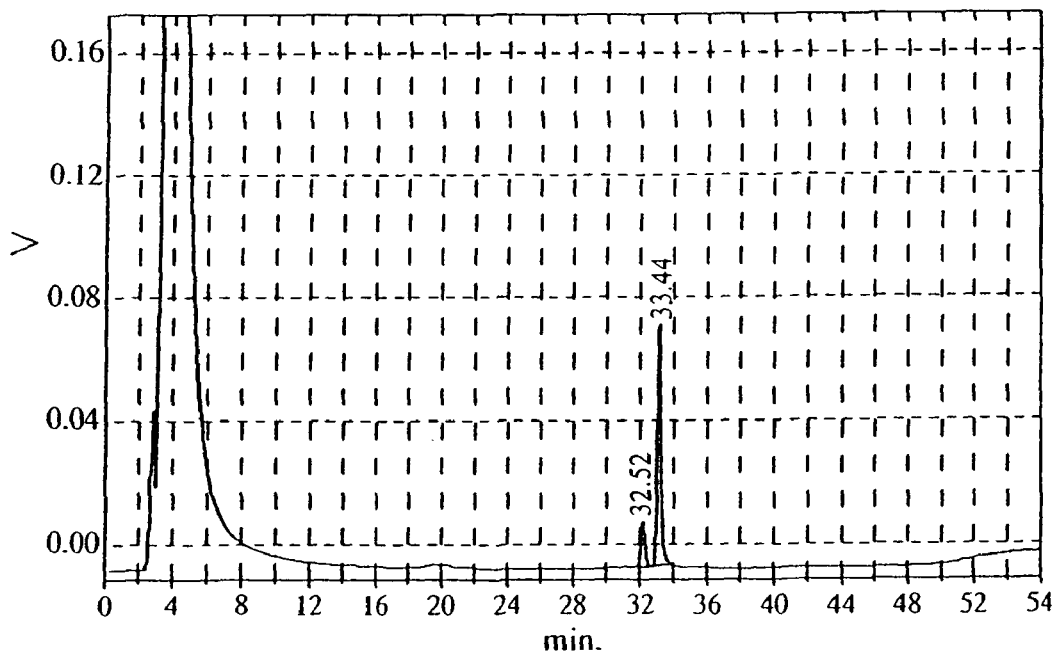
FIG. 3B is an HPLC trace of the reaction of Ac-Sox-Pro-Gly-Ser-Phe-Arg-Arg-Arg-NH$_2$ (SID No:1) (30 µM) by PKA after 12 min. at 30° C.
Figure 4B:
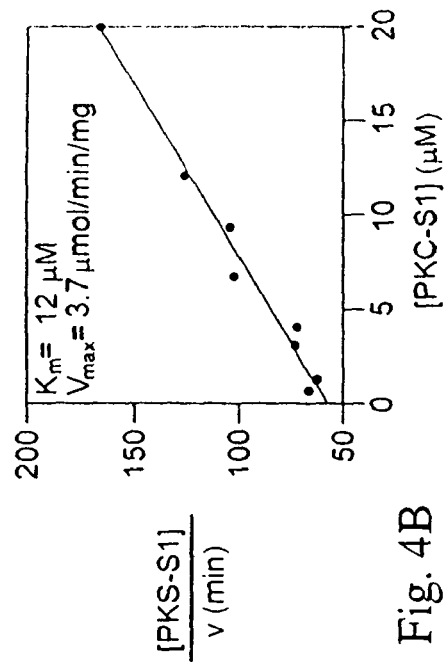
FIG. 4 are Hanes plots of Ac-Sox-Pro-Gly-Ser-Phe-Arg-Arg-Arg-NH$_2$ (SID No:1) reaction with PKC.
Figure 4D:
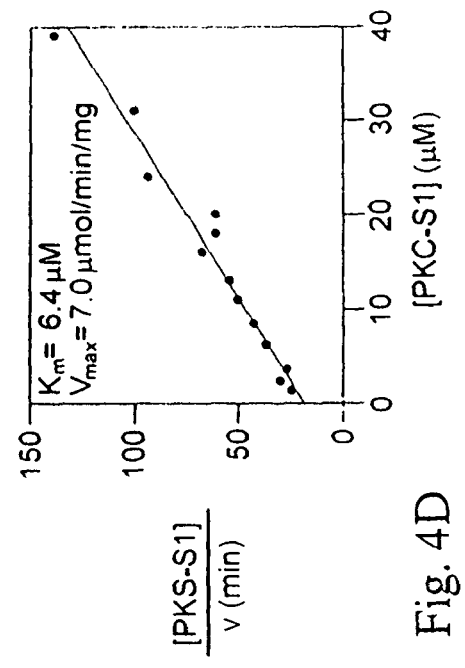
Figure 4A:
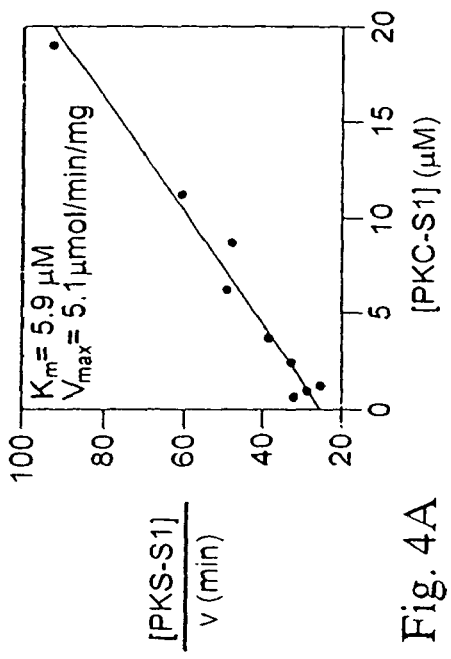
Figure 4C:
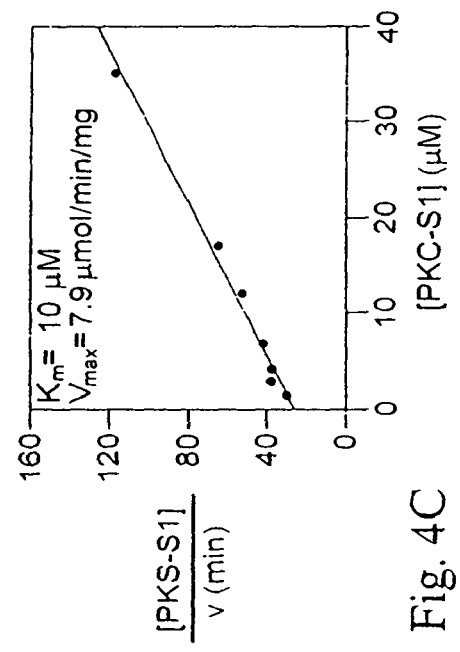
Figure 6B:
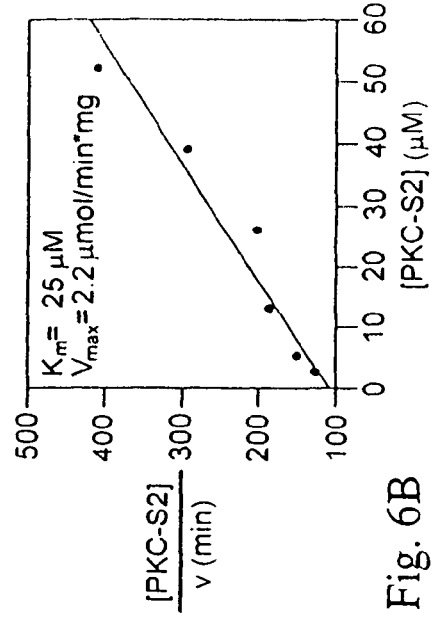
FIG. 6 are Hanes plots of Ac-Sox-Pro-Gly-Thr-Phe-Arg-Arg-Arg-NH$_2$ (SID No:3) with PKC.
Figure 6D:
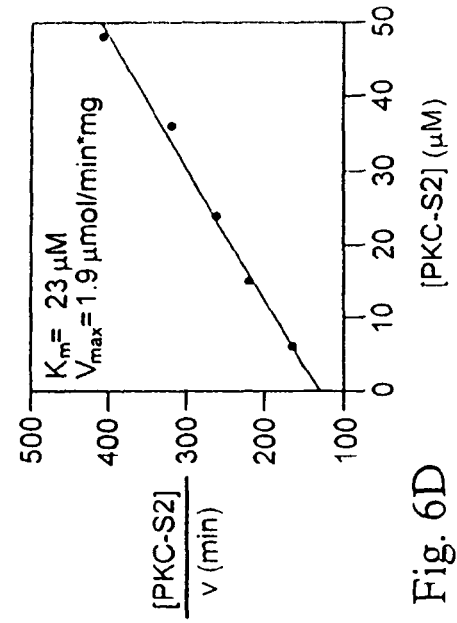
Figure 6A:
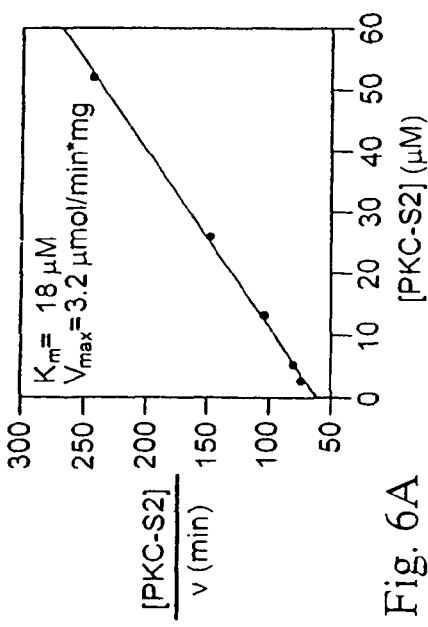
Figure 6C:
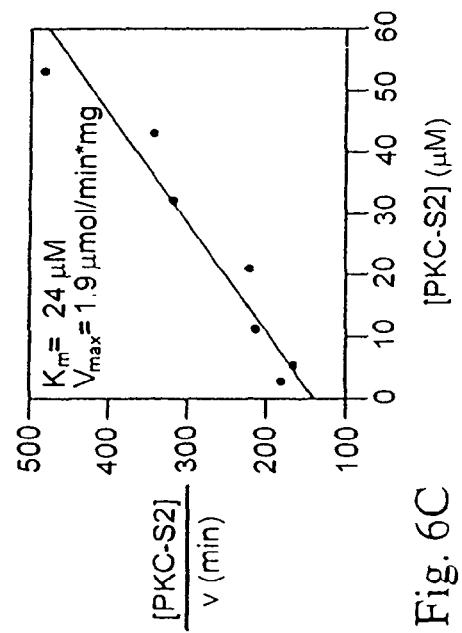

HPLC and MS Data for Kinase Reactions:

All reactions were followed in the fluorometer and quenched with 40 μl of a 0.1 M $Na_2$EDTA stock solution and then stored on ice. FIG. 3A depicts the phosphorylation of Ac-Leu-Arg-Arg-Ala-Ser-Leu-Pro-Sox-$NH_2$ (SID No:2) (7.8 μM) by PKA after 18 min. at 30° C. FIG. 3B depicts the phosphorylation of Ac-Sox-Pro-Gly-Ser-Phe-Arg-Arg-Arg- NH$_2$ (SID No:1) (30 μM) by PKA after 12 min. at 30° C. The HPLC peak identities for this peptide are shown below in Table 3.

Comparison of Fluorescence and HPLC Data Concerning Amount of Product Formed:

$$P(t) = \frac{I(t) - f_S S_0}{f_P - f_S}$$

| Kinase Reaction | Initial Substrate Conc. | Length of reaction | [Product] (μM) from fluorescence | [Product] (μM) from HPLC (228 nm) | [Product] (μM) from HPLC (280 nm) |
|---|---|---|---|---|---|
| PKA | 46 μM | 300 sec. | 1.6 | 1.3 | 1.9 |
| PKA | 7.8 μM | 700 sec. | 3.4 | 3.3 | 3.5 |
| PKA | 7.8 μM | 18 min. | 4.6 | 4.4 | 4.8 |
| PKC | 30 μM | 12 min. | 3.3 | 3.2 | 4.7 |

Hanes Plots:

FIG. 4 are Hanes plots of Ac-Sox-Pro-Gly-Ser-Phe-Arg-Arg-Arg-NH$_2$ (SID No:1) reaction with PKC. $K_m$ and $V_{max}$ values were determined using $f_{S,avg}$=1.1×105±0.3 units/μM and $f_{P,avg}$=6.3×105±1.0 units/μM.

FIG. 5 are Hanes plots of Ac-Leu-Arg-Arg-Ala-Ser-Leu-Pro-Sox-NH$_2$ (SID No:2) reaction with PKA. $K_m$ and $V_{max}$ values were determined using $f_{S,avg}$=2.5×10$^5$±0.1 units/μM and $f_{P,avg}$=9.9×10$^5$±0.2 units/μM.

FIG. 6 are Hanes plots of Ac-Sox-Pro-Gly-Thr-Phe-Arg-Arg-Arg-NH$_2$ (SID No:3) reaction with PKC. $K_m$ and $V_{max}$ values were determined for using Fs and Fp values determined the day of each experiment.

TABLE 3

HPLC peak identities of SID Nos. 1 and 2

| Kinase | HPLC Peak No. | $T_R$ (min.) | [M + xH]$^{x+}$ | Expected [M + xH]$^{x+}$ | Peptide Identification |
|---|---|---|---|---|---|
| PKA | 1 | 24.8[a] | 627.8 (2+) | 627.8 | Product (SID No. 2) |
| PKA | 2 | 26.1[a] | 587.8 (2+) | 587.8 | Substrate (SID No. 2) |
| PKC | 1 | 32.5[b] | 659.2 (2+) | 659.2 | Product (SID No. 1) |
| PKC | 2 | 33.4[b] | 413.2 (3+) | 413.2 | Substrate (SID No. 1) |

[a] C18; solvent A = water, 0.1% v/v TFA; solvent B = MeCN, 0.1% v/v TFA, 10 min. 0% B, linear gradient 0-10% B over 2 min. followed by linear gradient 10-50% B over 30 min.

[b] C18; solvent A = water, 0.1% v/v TFA; solvent B = MeCN, 0.1% v/v TFA, 10 min. 15% B followed by linear gradient 15-50% B over 30 min.

The invention claimed is:

1. A method for detecting kinase activity, comprising the steps of:
   (a) providing a peptide comprising:
      (1) a kinase recognition sequence containing a phosphorylation site;
      (2) a β-turn sequence; and
      (3) an amino acid of the formula (I):

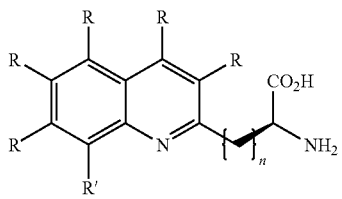

where each R is independently hydrogen or —SO₂X, wherein at
   least one R group is —SO₂X, where X is —OR" or —NR"R'";
   R' is hydroxy, amino, or thiol;
   R" is $C_{1-6}$ alkyl;
   R'" is hydrogen or alkyl; and
   n is 1, 2 or 3;
   (b) contacting the peptide with a sample comprising $Mg^{2+}$, a phosphate source, and a kinase; and
   (c) analyzing for the presence of a phosphorylated peptide product.

2. The method of claim 1, wherein the amino acid is of the formula (II):

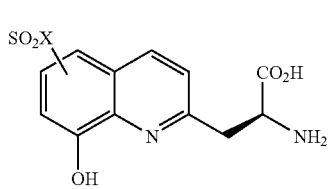

where X is —OR" or —NR"R'";
R" is $C_{1-6}$ alkyl; and
R'" is hydrogen or $C_{1-6}$ alkyl.

3. The method of claim 1, wherein the amino acid is of the formula (III):

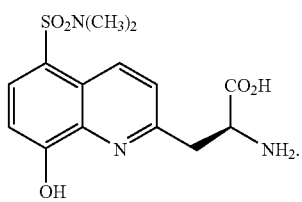

4. The method of claim 1, wherein fluorescence of the peptide increases by at least about 100% when bound to $Mg^{2+}$.

5. The method of claim 1, wherein the $K_m$ of the peptide for the kinase is in the micromolar range.

* * * * *

UNITED STATES PATENT AND TRADEMARK OFFICE
CERTIFICATE OF CORRECTION

PATENT NO. : 7,892,775 B2  
APPLICATION NO. : 11/801921  
DATED : February 22, 2011  
INVENTOR(S) : Barbara Imperiali et al.

It is certified that error appears in the above-identified patent and that said Letters Patent is hereby corrected as shown below:

Please delete the paragraph titled 'FEDERALLY SPONSORED RESEARCH OR DEVELOPMENT' encompassing column 1, lines 15-18:

"The subject matter of this application was developed in part with funding from the National Institute of Health (grant application no. GM64346). The government may have certain rights in this technology."

and replace with:

--This invention was made with government support under Grant No. U54 GM064346 awarded by the National Institutes of Health. The government has certain rights in this invention.--

Signed and Sealed this  
Twenty-third Day of October, 2012

David J. Kappos  
*Director of the United States Patent and Trademark Office*